United States Patent
Sakuragi (10) Patent No.: US 8,923,579 B2
(45) Date of Patent: Dec. 30, 2014

(54) SURGERY-ASSISTANCE APPARATUS, METHOD AND COMPUTER-READABLE RECORDING MEDIUM STORING A PROGRAM FOR SETTING A MARGIN DURING ORGAN EXCISION

(75) Inventor: Futoshi Sakuragi, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 288 days.

(21) Appl. No.: 13/220,353

(22) Filed: Aug. 29, 2011

(65) Prior Publication Data

US 2012/0053443 A1 Mar. 1, 2012

(30) Foreign Application Priority Data

Aug. 30, 2010 (JP) .................................. 2010-192200

(51) Int. Cl.
*G06K 9/00* (2006.01)
*G06T 7/00* (2006.01)
*A61B 19/00* (2006.01)
*A61B 17/00* (2006.01)

(52) U.S. Cl.
CPC ....... *A61B 19/50* (2013.01); *A61B 2017/00119* (2013.01); *G06T 7/0093* (2013.01); *G06T 2207/30101* (2013.01); *G06T 7/0081* (2013.01); *G06T 2207/10072* (2013.01); *A61B 2019/507* (2013.01); *G06T 2207/30061* (2013.01)
USPC ....................................................... 382/128

(58) Field of Classification Search
None
See application file for complete search history.

(56) References Cited

U.S. PATENT DOCUMENTS

2011/0093243 A1* 4/2011 Tawhai et al. ..................... 703/2

FOREIGN PATENT DOCUMENTS

| JP | 2001-137230 A | 5/2001 |
| JP | 2001-283191 A | 10/2001 |
| JP | 2002-345807 A | 12/2002 |
| JP | 2003-033349 A | 2/2003 |
| JP | 2007-054147 A | 3/2007 |
| JP | 2008-253293 A | 10/2008 |
| WO | WO 2010132606 A1 * 11/2010 | G09B 23/28 |

OTHER PUBLICATIONS

Beichel, Reinhard, and Dieter Schmalstieg. "Liver surgery planning using virtual reality." (2006).*
Reinhard Beichel, et al., "Liver Segment Approximation in CT Data for Surgical Resection Planning", Medical Imaging 2004: Image Processing, Proceedings of the SPIE, 2004, pp. 1435-1446, vol. 5370.

(Continued)

*Primary Examiner* — Nirav G Patel
(74) *Attorney, Agent, or Firm* — Sughrue Mion, PLLC (57) ABSTRACT

A dominance region in an organ dominated by a part of a structure is determined as a target region, and a region in the organ other than the target region is determined as a non-target region. The part of the structure extends from predetermined position v in a structure region toward a part of the organ, the part including a diseased part. Further, a margin region is set based on a distance from predetermined position v to each position on a boundary surface between the target region and the non-target region. The width of the margin region gradually increases from zero to a predetermined value in a range in which the distance is less than or equal to a predetermined threshold value, and the width of the margin region is substantially constant in a range in which the distance is greater than the predetermined threshold value.

11 Claims, 6 Drawing Sheets

(56) References Cited

OTHER PUBLICATIONS

Daisuke Kobayashi, et al., "Trial of Branch Base Tree Structure Model Construction for Blood Vessel Geometric Representation", RIKEN Symposium on Research on Digitization of Biological Sample's Shape and Construction of its Database, (URL:http://www.comp-bio.riken.jp/keijyo/products/2005_1_files/kobayashi_print.pdf), Mar. 9, 2005, pp. 84-92.

Sho Nakamura, et al., "Automated Classification of Pulmonary Artery and Vein from Chest X-ray CT images by Tree Structure Analysis", Technical Report of the Institute of Electronics Information and Communication Engineers, (URL:http://www.murase.nuie.nagoya-u.ac.jp/~ide/res/paper/J05-kenkyukai-snaka-1.pdf), Jan. 21, 2006, p. 105-108, vol. 105, No. 580.

Yasushi Hirano, et al., "Quantification of shrinkage of lung lobes in chest CT images using the 3D Voronoi division and application to tumor discrimination", Proceedings of the 20$^{th}$ Annual Conference of the Japanese Society of Medical Imaging Technology, (URL:http://mase.itc.nagoya-u.ac.jp/~hirano/Papers/JAMIT2001.pdf), Jul. 2001, pp. 315-316.

* cited by examiner

SURGERY-ASSISTANCE APPARATUS, METHOD AND COMPUTER-READABLE RECORDING MEDIUM STORING A PROGRAM FOR SETTING A MARGIN DURING ORGAN EXCISION

BACKGROUND OF THE INVENTION

1. Field of the Invention

The present invention relates to a surgery-assistance apparatus, method and program to assist doctors in determining excision regions in surgeries of organs, such as livers and lungs. Further, the present invention relates to a computer-readable recording medium that stores therein the surgery-assistance program.

2. Description of the Related Art

When a surgery is performed on a patient to remove a diseased part (affected part) of his/her organ, such as a liver and a lung or lungs, doctors need to appropriately determine a part to be removed, in advance, by performing diagnosis using images before the surgery.

Japanese Unexamined Patent Publication No. 2007-054147 (Patent Document 1) proposes a surgery-assistance apparatus. In Patent Document 1, blood vessels, a liver parenchyma, and a tumor part are extracted from an X-ray CT image of the liver of a patient. Further, a blood vessel that dominates a region to which the extracted tumor belongs is identified based on the positions of the core lines of the extracted blood vessels, the diameters of the blood vessels or the like. Accordingly, a blood vessel that supplies nutrition to the tumor is identified. Further, in the region dominated by the identified blood vessel, a region in which a relative distance between pixels constituting a blood vessel and pixels constituting the liver parenchyma is longer than a predetermined maximum relative distance value is displayed as an abnormal perfusion region that might have been erroneously identified due to a mass effect on the blood vessel or the like.

Meanwhile, even if a target region to be removed is determined before surgery by performing diagnosis using images, a margin region is generally added to the target region in a real surgery, and both of the target region and the margin region are removed. The size of the margin region added to the target region has been determined based on a judgment by each doctor. Doctors need to make such judgments every time of surgery, and that is time-consuming and imposes more work on doctors. Further, since such judgments differ among doctors, it has been impossible to determine appropriate margin regions in a stable and efficient manner. Therefore, regarding the size of a margin region to be added to a target region, a technique for assisting doctors by a computer is also requested.

SUMMARY OF THE INVENTION

In view of the foregoing circumstances, it is an object of the present invention to provide a surgery-assistance (medical-operation-assistance) apparatus, method and program for automatically setting an appropriate margin region, based on a dominance region (dominated region), when a target region of excision (resection, removal or the like) has been set. Further, it is another object of the present invention to provide a computer-readable recording medium that stores therein the surgery-assistance program. Further, it is still another object of the present invention to assist doctors (surgeons, radiologists, or the like), in diagnosis by presenting set margin regions to them so that they can easily judge whether the margin regions are appropriately set.

A surgery-assistance apparatus of the present invention is a surgery-assistance apparatus that sets a margin region with respect to a target region of excision in an organ including a diseased part to be removed, and the margin region being removed together with the target region, the apparatus comprising:

a medical image obtainment unit that obtains a medical image representing the organ including the diseased part to be removed;

an organ region extraction unit that extracts an organ region from the obtained medical image;

a structure region extraction unit that extracts, from the obtained medical image, a structure region representing a structure that dominates the organ;

a target region determination unit that determines a dominance region in the organ as the target region, and a region in the organ other than the target region, as a non-target region, and the dominance region being dominated by a part of the structure, the part extending from a predetermined position in the structure region toward a part of the organ, the part including the diseased part; and a margin region setting unit that sets, based on a distance from the predetermined position to each position on a boundary surface between the target region and the non-target region, the margin region to be added to the target region, wherein the margin region setting unit sets the margin region in such a manner that the width of the margin region gradually increases from zero to a predetermined value in a range in which the distance is less than or equal to a predetermined threshold value, and that the width of the margin region is substantially constant in a range in which the distance is greater than the predetermined threshold value.

Further, a surgery-assistance method of the present invention is a surgery-assistance method for setting a margin region to be added to a target region of excision in an organ including a diseased part to be removed, the method comprising the steps of:

obtaining a medical image representing the organ including the diseased part to be removed;

extracting an organ region from the obtained medical image;

extracting, from the obtained medical image, a structure region representing a structure that dominates the organ;

determining a dominance region in the organ as the target region, and a region in the organ other than the target region, as a non-target region, and the dominance region being dominated by a part of the structure, the part extending from a predetermined position in the structure region toward a part of the organ, the part including the diseased part; and setting, based on a distance from the predetermined position to each position on a boundary surface between the target region and the non-target region, the margin region to be added to the target region, wherein the margin region is set in such a manner that the width of the margin region gradually increases from zero to a predetermined value in a range in which the distance is less than or equal to a predetermined threshold value, and that the width of the margin region is substantially constant in a range in which the distance is greater than the predetermined threshold value.

Further, a non-transitory computer-readable recording medium or a computer-readable recording medium of the present invention has stored therein a surgery-assistance program for causing a computer to execute processing for assisting doctors in surgery.

In the present invention, a medical image is a three-dimensional anatomical image (3D Anatomical Image), which represents the structure of an organ three-dimensionally. Further, a three-dimensional functional image (3D Functional Image) may be obtained in addition to the 3D anatomical image. In the 3D functional image, evaluation values for evaluating the function of the organ are three-dimensionally arranged in the shape of the organ. Specifically, medical images are obtained from an internal memory or storage of a computer that functions as a surgery-assistance apparatus. Alternatively, medical images are obtained from an external storage directly connected to the computer, or an external storage connected to the computer through a network. The 3D functional image is volume data composed of voxel data representing evaluation values (for example, values representing the motion or physiological reactions of the organ) that are used to evaluate whether the function of the organ is normal. Meanwhile, the 3D anatomical image is volume data composed of voxel data representing the anatomical structure of the organ.

Further, the phrase "dominates the organ" means keeping the function of the organ normal by supplying oxygen and nutrition to the organ. For example, if the organ is a liver, a blood vessel or vessels correspond to a structure that dominates the organ. If the organ is a lung or lungs, a bronchus or bronchi correspond to a structure that dominates the organ. If the organ is a brain, a cerebral artery corresponds to a structure that dominates the organ.

Further, extraction of an organ region, extraction of a structure region, and extraction of a dominance region may be performed by calculation using a known method. For example, if the organ is a liver, a dominance region can be obtained by using the following method. First, blood vessels in the liver region are extracted, and blood vessels that dominate regions in the liver region (liver parenchyma or the like) other than the blood vessels are identified by using a Voronoi diagram. Accordingly, regions dominated by respective blood vessels are identified as liver segments (please refer to Japanese Unexamined Patent Publication No. 2003-033349, R Beichel et al., "Liver segment approximation in CT data for surgical resection planning", Medical Imaging 2004: Image Processing, Edited by Fitzpatrick, J. Michael; Sonka, Milan, Proceedings of the SPIE, Volume 5370, pp. 1435-1446, 2004, and the like).

If the region is a lung field, a dominance region may be determined by using the following method. First, a set of voxels in a bronchus region is extracted by using a region growing method, and thinning processing is performed on the extracted bronchus region. Further, voxels on the obtained thin lines representing bronchi are classified, based on the connection relationships between the thin lines, into end points, edges (sides) and branch points. Accordingly, tree structure data representing the bronchi are obtained (for details, please refer to "Trial of Branch Base Tree Structure Model Construction for Blood Vessel Geometric Representation" [on line], Daisuke Kobayashi, et al., RIKEN, RIKEN Symposium on Research on Digitization of Biological Sample's Shape and Construction of its Database, pp. 84-92, Mar. 9, 2005, [search conducted on Jan. 6, 2010], Internet (URL: http://www.comp-bio.riken.jp/keijyo/products/2005_1_files/kobayashi_print.pdf), "Automated Classification of Pulmonary Artery and Vein from Chest X-Ray CT Images by Tree Structure Analysis", Sho Nakamura, et al., Technical Report of the Institute of Electronics, Information and Communication Engineers (IEICE), MI, Medical Image, Japan, IEICE, Vol. 105, No. 580, pp. 105-108, Jan. 21, 2006 [search conducted on Nov. 20, 2009], Internet (URL:http://www.murase.nuie.nagoya-u.ac.jp/~ide/res/paper/J05-kenkyukai-snaka-1.pdf), and the like). Further, three-dimensional Voronoi division is performed by using, as a set of seed points, the obtained structure of the bronchus. The three-dimensional Voronoi division is performed to find out to which bronchus constituting the bronchus structure each voxel in a lung region is closest. In other words, the three-dimensional Voronoi division is performed to find out bronchi that dominate respective voxels in the lung region. Accordingly, a region dominated by the same bronchus is determined as a dominance region of the bronchus (for details, please refer to "Quantification of Shrinkage of Lung Lobes in Chest CT Images Using the 3D Voronoi Division and Application to Tumor Discrimination" [on line], Yasushi Hirano, et al., Proceedings of the 20th Annual Conference of the Japanese Society of Medical Imaging Technology, pp. 315, 316, July, 2001, [search conducted on Nov. 20, 2009], Internet (URL: http://mase.itc.nagoya-u.ac.jp/~hirano/Papers/JAMIT2001.pdf), and the like). Further, as other examples, Japanese Unexamined Patent Publication No. 2001-137230 and Japanese Unexamined Patent Publication No. 2008-253293 disclose techniques for extracting a lung field. Further, Japanese Unexamined Patent Publication No. 2001-283191 and Japanese Unexamined Patent Publication No. 2002-345807 disclose techniques for extracting a liver. These techniques are also applicable.

The "target region" is a dominance region in an organ, and the dominance region is dominated by a part of a structure such as a blood vessel, the part extending from a predetermined position in the structure region toward a part of the organ, the part including the diseased part to be removed in the surgery. For example, when a diseased part in a liver is removed by surgery, a part of a blood vessel that dominates the diseased part by supplying nutrition, oxygen and the like to the diseased part is identified, and a part of the liver dominated by the part of the blood vessel is determined as the target region. In this example, the part of the blood vessel extends from a position at which the blood vessel is ligated to be removed toward the organ side including the diseased part. In other words, the part of the blood vessel extends toward the distal end of the blood vessel from the position at which the blood vessel is ligated to be removed. Further, the "margin region" is added to the target region as described above. When a target region is removed in real surgery, the margin region is set so as to remove a region including some safety margin, and a region slightly larger than the target region is removed.

Further, a part of a structure, the part extending from a predetermined position in the structure region toward a part of the organ, the part including the diseased part to be removed, may be set by using various known techniques. For example, the technique disclosed in Japanese Unexamined Patent Publication No. 2001-283191 may be used. A structure may be displayed on a display device, and an input specifying a predetermined position in the structure by a manual operation of a user may be received. Further, a region extending from the predetermined position toward the organ including the diseased part may be set as the part of the structure.

The width (thickness) of the margin region is a width, in the direction of the normal at each point on a boundary surface between a target region and a non-target region to the boundary surface, from the points on the boundary surface. The width of the margin region is a positive value. Further, it is desirable that the value of the width of the margin region is settable by each doctor or the like. Further, a predetermined value is positive at least at one position on the boundary surface. It is desirable that the predetermined value is settable for the kind of a tumor to be removed, and for each doctor who performs the surgery, because the margin region differs depending on the kind of each tumor to be removed, and each doctor who performs the surgery. Further, for example, when plural target regions are present, it is desirable that a predetermined value is settable for each of the plural target regions.

Further, the expression "the width of the margin region gradually increases from zero to a predetermined value in a range in which the distance is less than or equal to a predetermined threshold value" means that the width of the margin region may increase in any manner as long as the width increases in the range in which the distance is less than or equal to the predetermined threshold value. For example, the width of the margin region may increase in proportion to a distance. Alternatively, the width of the margin region may increase in proportion to the square of a distance, or the width of the margin region may increase intermittently in apart of the range in which the width of the margin region is less than or equal to the predetermined threshold value. Alternatively, the width of the margin region may be defined by an arbitrary function of distance.

Further, the margin region setting unit may set the width of the margin region based on the following formula:

$$M(pt) = \begin{cases} \left(1 - \frac{D(pt, v)}{r}\right) \times M, & (D(pt, v) < r) \\ M, & (r \leq D(pt, v)) \end{cases} \quad \text{[Formula (1)]}$$

where

M(pt) is the width of a margin region, pt is a point on a boundary surface between a target region and a non-target region, v is a predetermined position on a structure, D(pt, v) is a distance from point pt on the boundary surface to predetermined position v on the structure, r is a threshold value, and M is a predetermined value.

It is desirable that a surgery-assistance apparatus of the present invention further includes a display control unit that makes a display device display the set margin region in an identifiable manner.

Further, a surgery-assistance apparatus of the present invention may further include a detection unit that detects the structure region included in the set margin region other than the part of the structure. When the detection unit is provided, it is desirable that the display control unit makes a display device display, in an identifiable manner, the detected structure region included in the set margin region other than the part of the structure. Further, when the detection unit is provided, a surgery-assistance apparatus of the present invention may include a warning unit that gives a warning based on detection of the structure region included in the set margin region other than the part of the structure.

When the detected structure region included in the set margin region other than the part of the structure is displayed in an identifiable manner, the structure region may be displayed in any manner as long as the structure region included in the set margin region other than the part of the structure is distinguishable from the other region of the structure. For example, the structure region included in the set margin region other than the part of the structure may be displayed in a different color from the other region, or in a blinking manner, or with a thick contour, or the like. Further, the warning unit may give a warning in any manner as long as users can recognize the warning. For example, the warning may be given by sound, or by display on a display screen.

Further, in a surgery-assistance apparatus of the present invention, the target region determination unit may determine, as the target region, both of the dominance region dominated by the part of the structure and a dominance region dominated by the detected structure region included in the set margin region other than the part of the structure. In this case, the target region determination unit sets, as a new target region, both of the dominance region dominated by the part of the structure, the part extending from a predetermined position in the structure region toward a part of the organ, the part including the diseased part to be removed, and the dominance region dominated by the detected structure region included in the set margin region other than the part of the structure. Further, the margin region setting unit may set a margin region with respect to the new target region.

In the surgery-assistance apparatus and method, and in a computer-readable recording medium of the present invention having stored therein a surgery-assistance program, the margin region is set based on a distance from a predetermined position to each position on a boundary surface between the target region and the non-target region. Specifically, the margin region is set in such a manner that the width of the margin region gradually increases from zero to a predetermined value in a range in which the distance is less than or equal to a predetermined threshold value, and that the width of the margin region is substantially constant in a range in which the distance is greater than the predetermined threshold value. Therefore, it is possible to automatically set an appropriate margin region based on a dominance region. Hence, doctors and radiology technicians can easily set a region of an organ that should be removed in a real surgery.

When the surgery-assistance apparatus of the present invention further includes a display control unit for making a display device display a set margin region in an identifiable manner, a region of an organ to be removed is easily recognizable. In the present invention, the set margin region is presented so that a doctor or the like can easily judge whether the margin region has been appropriately set. In this manner, the present invention assists a doctor or the like in determining an appropriate region to be removed.

When the surgery-assistance apparatus of the present invention further includes a detection unit for detecting a structure region included in a set margin region other than a part of the structure, and the display control unit displays, in an identifiable manner, the structure region included in the set margin region other than the part of the structure, it is possible to present information that a structure region that is not intended to be removed will be removed because the structure region is in the margin region, which will be removed. If such information is presented, a doctor can easily judge whether the margin region has been appropriately set. In this manner, the present invention assists a doctor or the like in determining an appropriate region to be removed.

When the surgery-assistance apparatus of the present invention further includes a detection unit for detecting a structure region included in a set margin region other than a part of the structure, and a warning unit for giving a warning based on detection of the structure region included in the set margin region other than the part of the structure, it is possible to present information that the structure region that is not intended to be removed will be removed because the structure region is included in the margin region, which will be removed. If such a warning is given, a doctor can easily judge whether the margin region has been appropriately set. In this manner, the present invention assists a doctor or the like in determining an appropriate region to be removed.

When the target region determination unit determines, as a target region, both of the dominance region dominated by the part of the structure and the dominance region dominated by the detected structure region included in the set margin region other than the part of the structure, the target region determination unit sets, as a new target region, both of the dominance region dominated by the part of the structure, the part extending from a predetermined position in the structure region toward a part of the organ, the part including the diseased part to be removed, and the dominance region dominated by the structure region included in the set margin region other than the part of the structure. Further, the margin region setting unit sets a margin region with respect to the new target region. Therefore, when the structure region that is not intended to be removed will be removed because the structure region is in the set margin region, which will be removed, a new margin region is automatically set. Therefore, the present invention assists a doctor or the like in determining an appropriate region to be removed.

Note that the program of the present invention may be provided being recorded on a computer readable medium. Those who are skilled in the art would know that computer readable media are not limited to any specific type of device, and include, but are not limited to: floppy disks, CD's RAM'S, ROM's, hard disks, magnetic tapes, and internet downloads, in which computer instructions can be stored and/or transmitted. Transmission of the computer instructions through a network or through wireless transmission means is also within the scope of this invention. Additionally, computer instructions include, but are not limited to: source, object and executable code, and can be in any language including higher level languages, assembly language, and machine language.

DESCRIPTION OF THE PREFERRED EMBODIMENTS

Hereinafter, a surgery-assistance apparatus, program and method according to embodiments of the present invention will be described in detail with reference to drawings.

In the following embodiments, a surgery-assistance apparatus 1 is realized by installing, in a computer, a surgery-assistance program according to respective embodiments of the present invention. The computer may be a workstation or a personal computer that is directly operated by a doctor who diagnoses a patient. Alternatively, the computer may be a server computer connected, through a network, to the workstation, the personal computer or the like. A surgery-assistance program is stored in a recording medium, such as a DVD and a CD-ROM, and distributed. Further, the surgery-assistance program is installed in a computer from the recording medium. Alternatively, the surgery-assistance program is stored in a storage device of a server computer connected to a network, or stored in a network storage accessibly from the outside. The surgery-assistance program is downloaded, based on a request for downloading, in a computer used by the doctor, and installed in the computer.

Figure 1:
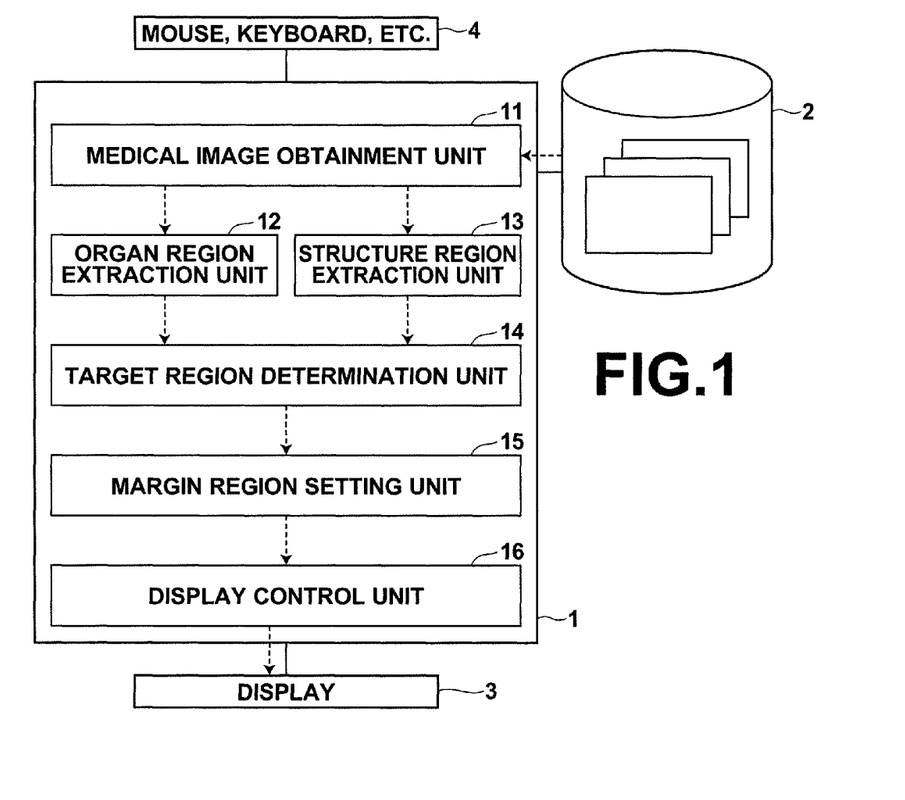
FIG. 1 is a schematic diagram illustrating the configuration of a surgery-assistance apparatus according to a first embodiment of the present invention.

FIG. 1 is a schematic diagram illustrating the configuration of the surgery-assistance apparatus 1, which is realized by installing a surgery-assistance program in a workstation. As FIG. 1 illustrates, the surgery-assistance apparatus 1 is configured as a standard workstation that includes a CPU (not illustrated) and a memory (not illustrated), and a storage 2 is provided. Further, a display (display device) 3, and an input device 4, such as a mouse, are connected to the surgery-assistance apparatus 1.

The storage 2 stores, as three-dimensional anatomical image v, volume data reconstructed from slice data output from a CT (Computed Tomography) apparatus or an MRI (Magnetic Resonance Imaging) apparatus, volume data output from an MS (Multi Slice) CT apparatus or a cone-beam CT apparatus, or the like. The volume data are obtained by performing plural times of imaging on a patient to be examined (a region to be examined or the like) at predetermined time intervals. The storage 2 stores a plurality of sets of time-series volume data for each patient or a region of each patient, or for each modality.

Further, the storage 2 stores, as three-dimensional functional image, a SPECT (Single Photon Emission Computed Tomography) image output from a SPECT apparatus, a functional image generated by analyzing volume data output from a MSCT (Multi-Slice Computed Tomography) apparatus, or the like.

The memory stores the surgery-assistance program and data (processing parameter or the like) to which the surgery-assistance program refers. The surgery-assistance program regulates, as processing executed by the CPU, medical image obtainment processing, organ region extraction processing, structure region extraction processing, target region determination processing, margin region setting processing, and display control processing. When the CPU executes these kinds of processing based on the program, the general-purpose workstation functions as a medical image obtainment unit, an organ region extraction unit, a structure region extraction unit, a target region determination unit, a margin region setting unit, and a display control unit.

FIG. 1 is a functional block diagram of the surgery-assistance apparatus 1. Each functional block will be described.

A medical image obtainment unit 11 obtains a medical image representing an organ including a diseased part to be removed. In the present embodiment, an X-ray CT image of the liver of a patient to be examined is used as a processing target image. When plural kinds of examination (for example, CT examination and SPECT examination) are performed on the patient, and consequently, both of three-dimensional anatomical image v and a three-dimensional functional image are stored in the storage 2, the two kinds of image are loaded in the memory. When only the three-dimensional anatomical image v is stored, only the three-dimensional anatomical image v is loaded.

An organ region extraction unit 12 extracts an organ region from the obtained medical image. In the present embodiment, the organ region extraction unit 12 calculates a feature value representing the likelihood of the contour of a liver with respect to each voxel data constituting the three-dimensional anatomical image. Further, the organ region extraction unit 12 evaluates, based on an evaluation function that has been obtained in advance by machine learning, the calculated feature values. In this manner, the organ region extraction unit 12 judges whether voxel data represent the contour of the liver. This judgment is repeated to extract voxel data representing the contour of the whole river. In this embodiment, an Ada-Boost algorithm is used to obtain the evaluation function. A liver region 5 may be extracted by using various kinds of known method as long as the organ can be extracted. Other machine learning methods and statistical analysis methods, for example, such as a linear discriminant method, a neural network and a support vector machine, may be used.

A structure region determination unit 13 extracts, from the obtained medical image V, a structure region 6 dominating the organ. The structure region determination unit 13 performs, on the liver region 5 extracted from the medical image V, blood vessel region extraction processing and tree structure detection processing. First, the eigenvalues of 3×3 Hessian matrix are calculated for respective local regions in the liver region 5 to explore the local regions for a linear structure. One of the three eigenvalues of the Hessian matrix is close to zero, and the other two eigenvalues are relatively large values. An eigenvector corresponding to the eigenvalue close to zero represents the main axial direction of the linear structure. In blood vessel region extraction processing, this relationship is used, and the likelihood of a linear structure is judged, based on the eigenvalues of the Hessian matrix, for each local region. Further, when a linear structure is discriminated in a local region, a center point in the local region is detected as a candidate point.

Further, candidate points detected by exploration are connected to each other based on a predetermined algorithm. Accordingly, tree structure 6A composed of the candidate points and blood vessel branches (edges) connecting the candidate points is constructed. Coordinate information about the plural candidate points that have been detected, and vector information representing the directions of the blood vessel branches are stored in the memory together with the identifiers of the candidate points and the blood vessel branches. Then, the contour of a blood vessel (the outer wall of a blood vessel) is identified for each of the detected candidate points in a cross section of the blood vessel perpendicular to the path of the blood vessel. The contour of the blood vessel is identified based on the values (CT values) of voxels in the vicinity of each of the detected candidate points. The shape is identified by using a known segmentation method, typified by a Graph-Cuts method. Through the process as described above, information that is necessary to identify the extracted blood vessel region is generated, and stored in the memory.

The target region determination unit 14 determines, as a target region, a dominance region in an organ. The dominance region dominated by a part of the structure, the part extending from a predetermined position in the structure region toward a part of the organ, the part including the diseased part, is determined as the target region. Further, the target region determination unit 14 determines, as a non-target region, a region in the organ other than the target region.

Specifically, first, the target region determination unit 14 determines, based on the extracted organ region 5 and the extracted structure region 6, a dominance region dominated by the structure. In the present embodiment, the dominance region is determined by using a method disclosed in Japanese Unexamined Patent Publication No. 2003-033349. Specifically, blood vessels in the liver region are extracted, and blood vessels that dominate regions in the liver region (liver parenchyma or the like) other than the blood vessels are identified by using a Voronoi diagram. Various kinds of other known method may be used as long as a dominance region is determined.

Further, the target region determination unit 14 sets a part of the structure that dominates a part of the organ, the part including the diseased part to be removed. Hereinafter, in this specification, a part of a structure that dominates a part of an organ, the part including a diseased part to be removed, is also called as a partial region. A partial region 61 may be set by using various kinds of known method. In the present embodiment, a structure is displayed on a display, and an input of data specifying position v on a blood vessel by manual operation of a user at an input device, such as a mouse, is accepted. Further, a part extending from the specified position toward the organ including the diseased part is set as the partial region 61. The partial region 61 may be set automatically by using a known technique, such as the technique disclosed in Japanese Unexamined Patent Publication No. 2001-283191.

Further, the target region determination unit 14 determines, as a target region 51, the dominance region dominated by the partial region 61.

The margin region setting unit 15 sets the margin region based on a distance from predetermined position v to each position pt on a boundary surface between the target region 51 and the non-target region 53. The margin region is set in such a manner that the width of the margin region gradually increases from zero to predetermined value M in a range in which the distance is less than or equal to predetermined threshold value r, and that the width of the margin region is substantially constant in a range in which the distance is greater than the predetermined threshold value r. In the present embodiment, the margin region is set by using the formula (1), which will be described later.

It is not necessary that the formula (1) is used. The width of the margin region may increase in any mariner as long as the width of the margin region gradually increases from zero to a predetermined value in a range in which the distance is less than or equal to a predetermined threshold value. For example, the width of the margin region may increase in proportion to the square of a distance, or the width of the margin region may increase intermittently in a part of the range in which the width of the margin region is less than or equal to a predetermined threshold value. Alternatively, the width of the margin region may be defined by using an arbitrary function of distance. It is desirable that the width of the margin region is set so that the cut surface of a liver becomes smooth after resection. It is desirable that the width of the margin region is set so that a boundary surface between the margin region and a region that is not removed continues smoothly.

The display control unit 16 makes the display 3 display the set margin region in an identifiable manner. In the present embodiment, the target region 51 is displayed as a transparent area, and the margin region 52 is displayed as a semi-transparent area by setting a predetermined degree of transparency. Further, the non-target region 53 other than the margin region 52 is displayed as a colored opaque area.

Figure 2:
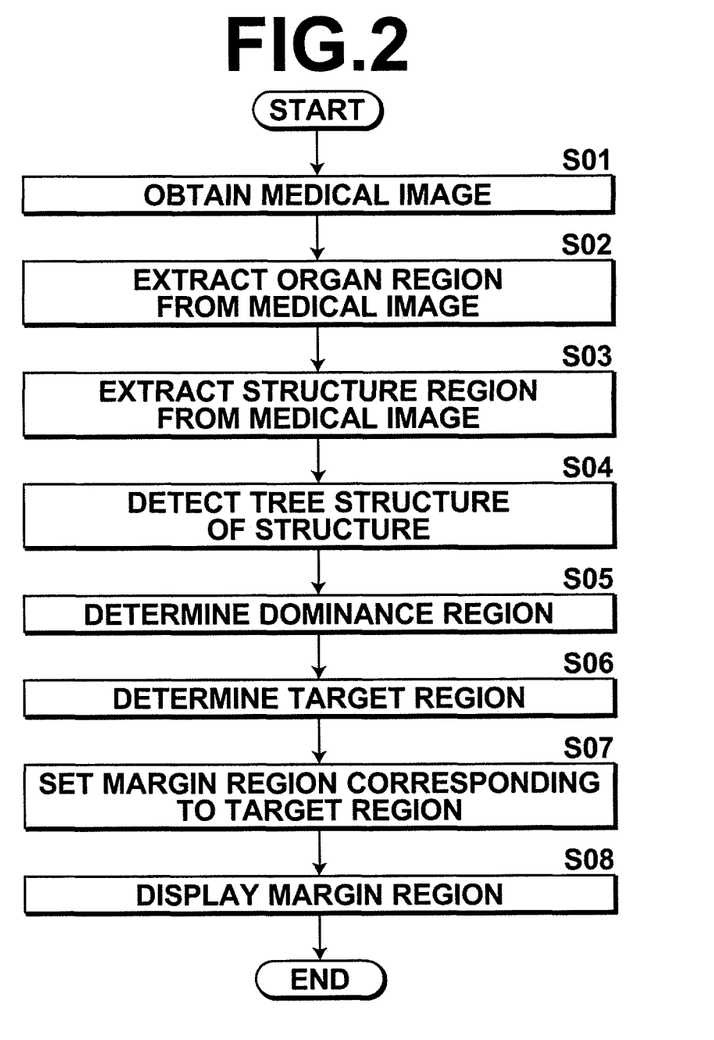
FIG. 2 is a flow chart of processing performed by the surgery-assistance apparatus according to the first embodiment.

FIG. 2 is a flow chart explaining the flow of surgery-assistance processing in the present embodiment. The surgery-assistance processing according to the present embodiment will be described with reference to FIG. 2.

First, when the medical image obtainment unit 11 detects selection of a surgery-assistance function according to the present embodiment in a selection menu, the medical image obtainment unit 11 displays a list of ID's of patients to be examined (or regions of the patients). When the surgery-assistance apparatus 1 detects a selection operation by a user, the surgery-assistance apparatus 1 loads an image file related to the selected patient or region to be examined into a memory (step S01).

When medical image V, which is a three-dimensional anatomical image, is loaded into the memory, the organ region extraction unit 12 extracts a liver region 5 from the medical image V (step S02).

Then, the structure region extraction unit 13 extracts, from the obtained medical image V, a structure region 6 dominating the organ (step S03). In the present embodiment, a blood vessel region 6 that dominates the liver is extracted. Further, the target region determination unit 14 constructs a tree structure 6A composed of blood vessel branches in the extracted blood vessel region 6 (step S04). The surgery-assistance apparatus 1 may perform the organ region extraction processing on the medical image V in step S02 and the structure extraction processing in steps S03 and S04 in parallel.

Next, the target region determination unit 14 determines, based on the extracted liver region 5 and the extracted blood vessel region 6, a dominance region dominated by each of blood vessel branches constituting the blood vessel region 6 (step S05).

Figure 3:
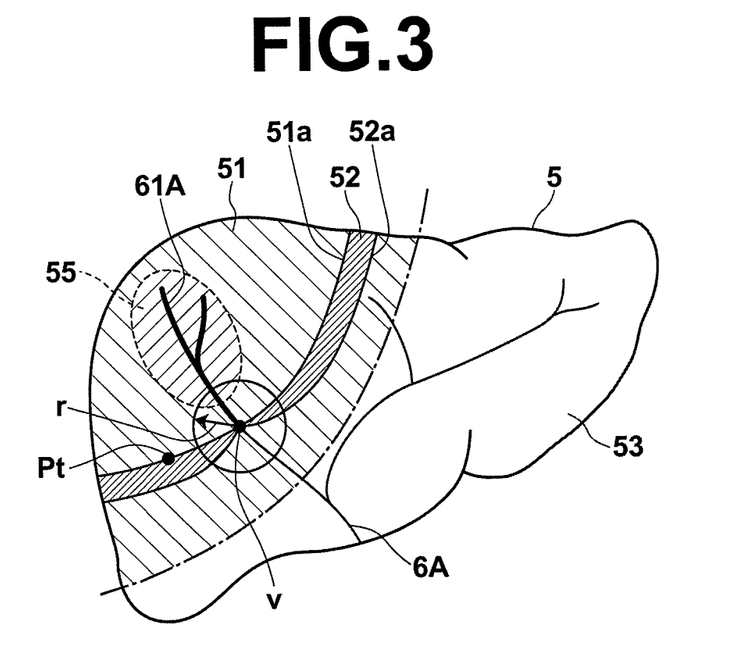
FIG. 3 is a diagram for explaining processing for setting a margin region in the first embodiment (a partial cross section of a liver)

FIG. 3 is a diagram explaining processing for determining a margin region. FIG. 3 is a partial cross section of a liver schematically illustrating the determined target region 51 and the tree structure 6A of blood vessels. The target region 51 includes a diseased part 55. In the present embodiment, the target region determination unit 14 outputs the detected tree structure 6A on the display screen of the display 3 after the steps as described above are performed. When the user specifies arbitrary position v in the tree structure 6A by using an input device 4, such as a mouse, the surgery-assistance apparatus 1 determines, based on the specified position v, a partial region 61 of a blood vessel. In the present embodiment, a region of blood vessel corresponding to a blood vessel branch 61A from the point v specified by the user to the end of the blood vessel branch 61A is determined as the partial region 61. The result of determining the partial region 61 is stored in the memory as volume data. In FIG. 3, the part 61A of the tree structure of the blood vessel corresponding to the partial region 61 is drawn with bold lines.

As illustrated in FIG. 3, the target region determination unit 14 determines, as the target region 51, a dominance region dominated by the partial region 61. Further, the target region determination unit 14 determines, as the non-target region 53, a region of the liver parenchyma 5 other than the target region 51 (step S06).

Then, as illustrated in FIG. 3, the margin region setting unit 15 sets the margin region 52 corresponding to the target region 51.

In the present embodiment, the margin region setting unit 15 determines width M (pt) of the margin region 52 based on the boundary surface 51a between the target region 51 and the non-target region 53. Specifically, the margin region setting unit 15 determines the width M(pt) of the margin region 52 by using the formula (1) based on a distance between pixel pt on the boundary surface 51a and specified position v. The margin region setting unit 15 repeats processing on respective pixels on the boundary surface 51a of the target region 51 to determine the width M(pt) of the margin region 52. Accordingly, the non-target-region-side boundary surface 52a of the margin region 52 is set. Consequently, the margin region 52 is specified. Here, the width (thickness) of the margin region is a width, in the direction of the normal at each point on the boundary surface 51a between the target region 51 and the non-target region 53 to the boundary surface 51a, from the position pt of each pixel on the boundary surface 51a. The width of the margin region is a positive value. The width of the margin region is settable by each doctor. Further, the predetermined value is a positive value at least at one position on the boundary surface. The predetermined value is settable for the kind of a tumor to be removed, and for each doctor.

After then, the margin region setting unit 16 stores the determined margin region in the memory and the storage 2, and outputs the determined margin region by outputting the determined margin region, for example, to a display device (monitor display), a printer device (printout), a data recording device (recording on a medium), or the like.

Further, as illustrated in FIG. 3, the display control unit 16 displays the margin region 52 on the display 3 in an identifiable manner (step S08). In FIG. 3, the target region 51 is displayed as a transparent area, and the margin region 52 is displayed as a semi-transparent area. Further, the non-target region 53 other than the margin region 52 is displayed as a colored opaque area.

In the first embodiment of the present invention, the margin region is set based on a distance from a predetermined position to each position on a boundary surface between the target region 51 and the non-target region 53. The margin region is set in such a manner that the width of the margin region gradually increases from zero to predetermined value M in a range in which the distance is less than or equal to a predetermined threshold value, and that the width of the margin region is substantially constant in a range in which the distance is greater than the predetermined threshold value. Therefore, it is possible to automatically set an appropriate margin region based on the target region. Hence, doctors and radiology technicians can easily set a region of an organ that should be removed in a real surgery. When the margin region is set by using the formula (1), it is possible to calculate the margin region by simple calculation, and an unnecessary load of calculation does not increase.

Further, in the first embodiment of the present invention, the display control unit 16 that makes the display device display the set margin region 52 in an identifiable manner is further provided. Therefore, it is possible to easily recognize the region of the organ to be removed. Further, the set margin region is presented so that the doctor can easily judge whether the set margin region is appropriate. In this manner, the present invention assists the doctor or the like in determining an appropriate resection region.

Further, in a modified example of the first embodiment of the present invention, a volume calculation unit (not illustrated) may be provided. The volume calculation unit automatically calculates the volume of each of the margin region 52 obtained by the processing in the first embodiment, the target region 51, and a part of the liver that remains after excision. It is desirable that the display control unit 16 displays the volumes on the display 3. When the volumes of the margin region 52, the target region 51, and the part of the liver that remains after excision are displayed, reference information for setting an appropriate range of margin region can be presented. Therefore, it is possible to assist a user in easily setting an appropriate margin region.

Further, in another modified example of the first embodiment of the present invention, plural predetermined values $M_i = M \times i/n$ ($0 < i \leq n$, n is a natural number) may be set as predetermined value M in the formula (1). The plural predetermined values $M_i$ are obtained by dividing the predetermined value M at predetermined sampling intervals. Further, the margin region setting processing in the first embodiment may be performed by using the formula (1) with respect to each of the plural predetermined values $M_i$. Further, it is desirable that information specifying each margin region that is set for each of plural predetermined values Mi, which are different from each other, is stored in advance in the storage 2 or the like. Further, it is desirable that an input at the display screen by a manual operation of a user, such as dragging an arbitrary position on the non-target-region-side boundary surface 52a of the margin region 52 by using a mouse, is acceptable. Further, it is desirable that the dragged position on the boundary surface 52a is detected, and that a margin region 52 of the plural different margin regions, the width of which corresponds to the dragged position, is displayed in a switching manner based on the width of the margin region at the dragged position on the boundary surface 52a. When an operation by the user is detected, and plural different margin regions are displayed synchronously with the operation by the user, it is possible to present reference information for setting an appropriate range of margin region. Therefore, it is possible to assist a user in easily setting an appropriate margin region.

It is desirable that information specifying each margin region that is set for each of plural different predetermined values Mi is stored in the storage 2 or the like in advance, as described above. When such information is stored in advance, it is possible to display the margin region in a switching manner synchronously with the operation by the user, more promptly than the case of setting each corresponding margin region after accepting an operation, such as dragging, by a user.

In this case, the aforementioned volume calculation unit may be further provided, and the volumes of the displayed margin region 52, the target region 51, and the part of the liver that remains after excision may be displayed synchronously with the operation by the user, in addition to the margin region that is displayed in a switching manner. When margin regions having plural different widths are set, it is possible to make the user efficiently recognize the reference information for setting an appropriate range of margin region. Hence, it is possible to assist the user in easily setting an appropriate margin region. Further, the predetermined value M in the formula (1) may be changed, and a margin region that can leave, after excision, ⅓ of the whole liver in volume may be calculated as the maximum margin region. Further, the maximum margin region may be displayed in an identifiable manner. Generally, it is desirable that the part of the liver that remains after excision is greater than or equal to ⅓ of the whole liver. Therefore, it is possible to present reference information for setting an appropriate range of margin amount. Hence, it is possible to assist a user in setting an appropriate margin region.

Figure 4:
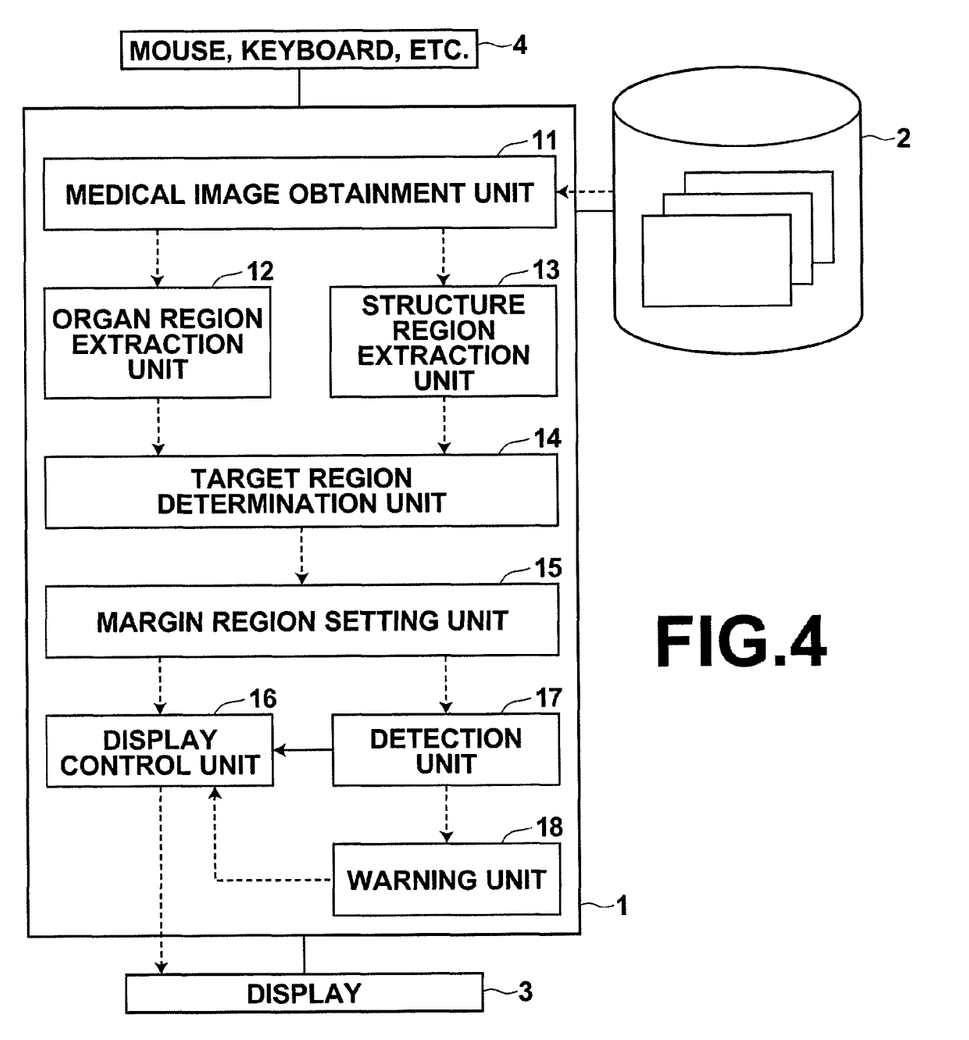
FIG. 4 is a schematic diagram illustrating the configuration of a surgery-assistance apparatus according to a second embodiment of the present invention.
Figure 5:
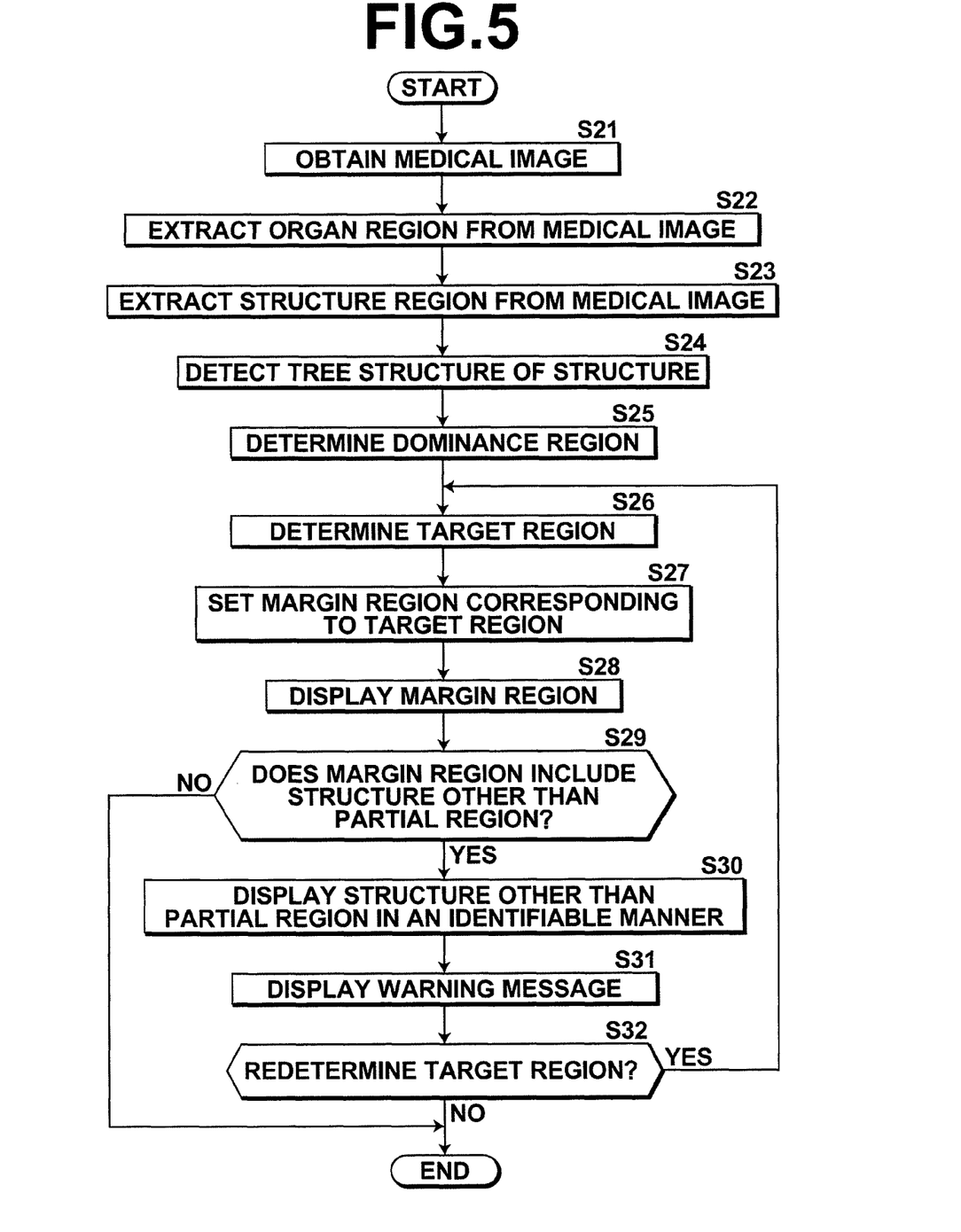
FIG. 5 is a flow chart of processing performed by the surgery-assistance apparatus according to the second embodiment.
Figure 6A:
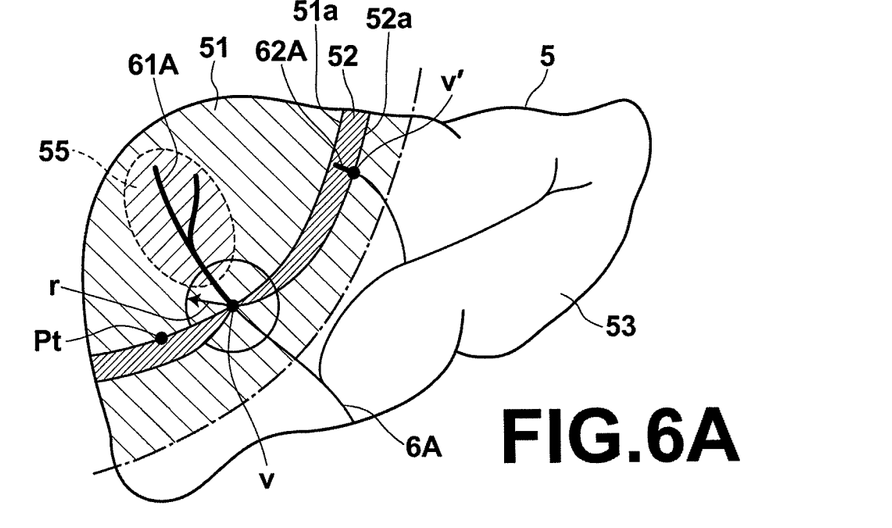
FIG. 6A is a diagram for explaining processing for setting a margin region in the second embodiment (No. 1)
Figure 6B:
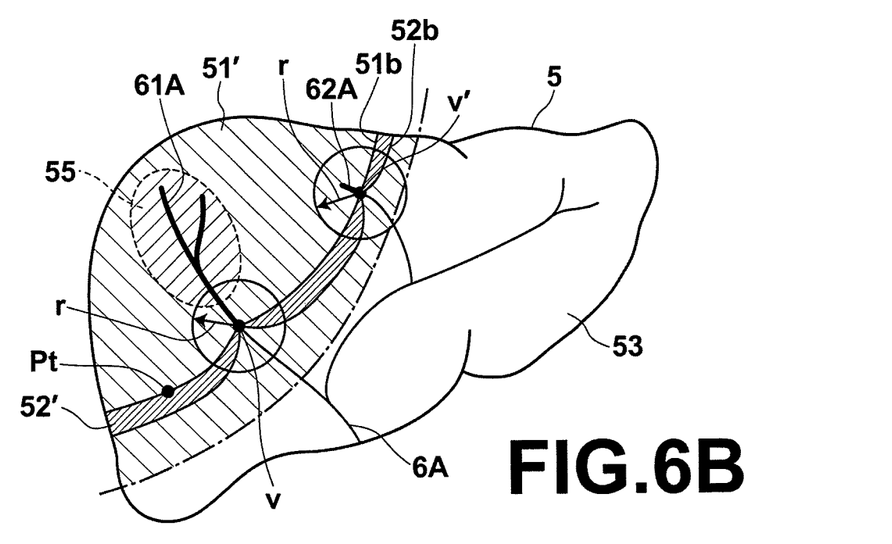
FIG. 6B is a diagram for explaining processing for setting a margin region in the second embodiment (No. 2).

FIG. 4 is a functional block diagram in a second embodiment. FIG. 5 is a flow chart illustrating the flow of processing in the second embodiment. FIGS. 6A and 6B are diagrams explaining processing for determining a margin region in the second embodiment. FIGS. 6A and 6B are partial cross sections of livers schematically illustrating the determined target regions 51, 51' and the tree structure 6A of blood vessels. Processing in the second embodiment will be described with reference to FIGS. 4 through 6B. In the second embodiment, a detection unit 17 and a warning unit 18 are provided in addition to the elements illustrated in the functional block diagram of the first embodiment. The detection unit 17 detects a structure region included in the margin region 52 other than the partial structure 61, which includes a different part of the blood vessel. With respect to the second embodiment, elements and features different from the first embodiment will be mainly described, and explanation on the same elements and features as those of the first embodiment will be omitted.

The detection unit 17 detects a structure region 62 included in the set margin region 52 other than the part 61 of the region (partial region 61). Since the margin region 52 and the blood vessel region 6 have been extracted already, the detection unit 17 detects, as a new structure region 62, a part of the blood vessel region 6 included in the margin region 52 other than the partial region 61. In the present embodiment, as illustrated in FIG. 6A, a blood vessel branch 62A that extends from a different branch of the tree structure 6A of blood vessels is included in the margin region 52 besides the blood vessel branch 61A corresponding to the partial region. A blood vessel region 62 corresponding to the blood vessel branch 62A is the structure region 62 included in the set margin region 52 other than the part 61 of the structure (partial region 61). In the present embodiment, the display control unit 16 displays, on the display 3, an indicator or the like representing the newly detected structure region 62 in an identifiable manner. Specifically, the part 62A of the tree structure corresponding to the structure region 62 is displayed in a blinking manner. Further, the color of the part 62A of the tree structure is changed to a different color so that the part 62A is identifiable.

The warning unit 18 presents a warning based on detection of the structure region 62 included in the margin region 52 other than the part 61 of the structure. In the present embodiment, the warning unit 18 gives a warning by making the display control unit 16 display a warning message on the display screen. The warning may be output to the outside by outputting a warning sound or voice, besides the aforementioned method. Alternatively, the warning may be given both by superimposing a warning message and by outputting a warning sound or the like. The warning unit 18 may instruct the display control unit 16 to display the part 62A of the tree structure representing the structure region 62 in a blinking manner, and to change the color of the part 62A of the tree structure to a different color so that the part 62A is identifiable.

Further, in the second embodiment, the target region determination unit 14 determines, as the target region 51, a dominance region dominated by the detected structure region 62 included in the margin region other than the part 61 of the structure and a dominance region dominated by the part 61 of the structure. Specifically, as illustrated in FIG. 6B, the target region determination unit 14 further sets, as a new target region 51', a dominance region dominated by the part 61 of the structure region and a dominance region dominated by the part 62 of the structure, other than the partial region 61. The part 61 of the structure region extends from predetermined position v in the structure region 6 toward a part of the organ including the diseased part 55. Further, the margin region setting unit 15 sets a margin region 52' for the new target region 51'.

Next, with reference to FIG. 5, surgery-assistance processing according to the second embodiment will be described. In the second embodiment, steps S21 through S28 in FIG. 5, which are similar to steps S01 through S08 in FIG. 2, are performed. The processing in steps S26 and S27 differ from steps S06 and S07 only when an instruction for redetermining a target region is received and processing for redetermining the target region is performed, as will be described later (step S32 is Y (YES)). Processing in such a case will be described later.

After the processing in steps S21 through S28 is performed, the detection unit 17 detects the structure region 62 included in the margin region 52 other than the part 61 of the structure (partial region 61). Further, as illustrated in FIG. 6A, when the structure region 62 corresponding to the blood vessel branch 62A is detected (step S29 is Y (YES)), the display control unit 16 displays the structure region 62 on the display 3 in an identifiable manner (step S30). Further, the warning unit 18 displays a warning message on the display 3 (step S31). The processing in step S30 and the processing in step S31 may be performed at the same time, or either one of the steps may be performed first.

In the present embodiment, when the structure region 62 corresponding to the blood vessel branch 62A is detected, the target region determination unit 14 makes the display control unit 16 display data or a message to ask for an instruction as to whether a target region should be redetermined. When an instruction to redetermine the target region is received by an input by a user at an input device, such as a mouse (step S32 is Y (YES), processing from step S26 is performed again.

Specifically, the target region determination unit 14 determines, as the target region 51', a dominance region dominated by the detected structure region 62 included in the margin region other than the part 61 of the structure and a dominance region dominated by the part 61 of the structure (step S26). In other words, as illustrated in FIG. 6B, an intersection between the detected blood vessel branch 62A in the structure region included in the margin region other than the partial region 61 and the boundary surface 51a between the target region 51 and the non-target region 53 is set as specified position v'. Further, the structure region 62 extending from the newly specified position v' toward the tip of the blood vessel branch is set as a new partial region 62. A dominance region dominated by the partial region 61 and a dominance region dominated by the new partial region 62 are determined as a new target region 51'. Further, a region other than the target region 51' is determined as a non-target region 53'. The target region determination unit 14 stores information specifying the target region 51' and the non-target region 53' in the memory.

As a method for setting dominance regions dominated by plural partial regions, various known methods may be adopted. Further, the dominance regions dominated by plural partial regions may be set as a target region by simply combining the dominance regions. Alternatively, a region may be obtained by performing correction processing, such as calculating a minimum region including the dominance regions dominated by the plural partial regions, and the obtained region may be set as the target region. Alternatively, a dominance region dominated by each of the plural partial regions may be set as a target region. Various methods may be used to set dominance regions, as long as the methods are based on dominance regions dominated by plural partial regions.

Then, the margin region setting unit 15 sets a margin region 52' for the new target region 51' by using the formula (1) (step S27). Specifically, the width M(pt) of the margin region 52' is set based on a distance from pixel pt on the boundary surface 51b between the target region 51' and the non-target region 53' to specified position v (or v'). The width M(pt) of the margin region 52' is determined by using the formula (1). When plural specified positions v, v' are present as in the present embodiment, the width M(pt) of the margin region 52' is determined based on the smaller one of a distance between pixel pt on the boundary surface 51b and the specified position v and a distance between the pixel pt on the boundary surface 51b and the specified position v'. Processing for determining the width M(pt) of the margin region 52' is repeated on each pixel on the boundary surface 51b of the target region 51'. Accordingly, a non-target-region-side boundary surface 52b of the margin region 52' is set. In this manner, the margin region 52' is specified. Further, the target region determination unit 14 stores information specifying the margin region 52' in the memory.

Further, the display control unit 16 displays the new margin region 52', which is redetermined, on the display 3 in an identifiable manner (step S28).

Meanwhile, when an instruction is input by the user through the input device, such as a mouse, that a target region is not redetermined (step S32 is N (NO)), processing ends. When the margin region 52 does not include a structure other than the partial region 51 (step S29 is N (NO)), processing also ends.

As described above, in the second embodiment, the surgery-assistance apparatus 1 further includes the detection unit 17 for detecting a structure region included in the set margin region other than the part of the structure. Further, the display control unit 16 displays the detected structure included in the set margin region other than the part of the structure in an identifiable manner. Therefore, it is possible to present information that the structure region that is not intended to be removed will be removed because the region is included in the set margin region, which will be removed. Therefore, a doctor can easily judge whether the margin region has been appropriately set. In this manner, the present invention assists a doctor or the like in determining an appropriate region to be removed.

In the second embodiment, the surgery-assistance apparatus 1 further includes the warning unit 18 for presenting a warning based on detection of a structure region included in the margin region other the part of the structure. Therefore, the aforementioned advantageous effects are achievable also by the warning unit 18. It is possible to more noticeably present information that the structure region that is not intended to be removed will be removed to the doctor or the like.

Further, the target region determination unit 14 determines, as the target region, a dominance region dominated by the detected structure region 62 included in the margin region other than the part 61 of the structure and a dominance region dominated by the part 61 of the structure. Therefore, the target region determination unit 14 sets, as a new target region 51', the dominance region dominated by the part 61 of the structure, the part extending from predetermined position v in the structure region 6 toward a part of an organ, the part including a diseased part 55, and the dominance region dominated by the structure region 62, other than the partial region 61. Further, the margin region setting unit 15 sets a margin region 52' with respect to the new target region 51'. Therefore, when a structure region that is not intended to be removed will be removed as the part 61 of the structure removed by the set margin region 52, it is possible to automatically set (reset) a new margin region 52'. Hence, it is possible to assist a doctor or the like in determining an appropriate region to be removed.

In the second embodiment, an appropriate limit may be provided in resetting of the margin region. For example, when a part of a liver is removed, generally, it is desirable that the remaining part of the liver after excision is greater than or equal to ⅓ of the whole liver in volume. Therefore, for example, a limit may be set in such a manner that if the non-target region of the liver other than the margin region, in other words, a region that is not removed by excision is less than ⅓ of the whole liver, resetting of the margin region is stopped.

In the second embodiment, it is not necessary to ask for an instruction as to whether resetting of a margin region should be performed. Resetting of the margin region may be repeated until no structure region included in the margin region other than the partial region is further detected. In this case, the margin region 52' is automatically reset so that a new structure region other than the partial region is not included in the margin region 52'. Therefore, it is possible to assist a doctor or the like in determining an appropriate region to be removed.

Further, in the surgery-assistance apparatus 1 in each of the embodiments, plural target regions may be determined for an organ, and margin region setting processing disclosed in this specification may be performed on each of the plural target regions.

Further, in the surgery-assistance apparatus 1 in each of the embodiments, it is desirable that the organ region extraction unit 12 displays an extracted organ region on a display screen of a display device, and detects an operation performed by a user on the display screen, and updates the organ region based on the detected operation. It is desirable that the structure region extraction unit 13 displays an extracted structure region on the display screen of the display device, and detects an operation performed by a user on the display screen, and corrects the extracted structure region based on the detected operation. Further, it is desirable that the target region determination unit 14 displays the determined target region on the display screen of the display device, and detects an operation performed by a user on the display screen, and updates the target region based on the detected operation. Further, it is desirable that the margin region setting unit 15 displays a set margin region on the display screen of the display device, and detects an operation performed by a user on the display screen, and corrects the extracted margin region based on the detected operation. Further, when the organ region or the structure region is corrected, it is desirable that the target region determination unit 14 determines a target region and a non-target region based on the corrected organ region or the structure region. Further, when the target region is corrected, it is desirable that the margin region setting unit 15 sets a margin region based on the set target region. Processing as described above is desirable, because the image quality of a three-dimensional anatomical image is low in some cases, and accurate extraction or estimation by a computer is impossible in such cases.

In each of the embodiments, the surgery-assistance apparatus 1 is realized by installing each program in a computer. Alternatively, programs may be installed in plural computers in a distributed manner to configure a surgery-assistance system that has a function similar to the surgery-assistance apparatus 1.

In each of the embodiments, the surgery-assistance apparatus 1 may include a means for outputting a print or data (recording data in a medium, such as a CD-R and DVD, or transferring data through a network), besides outputting data on a display. Specifically, in the present invention, the manner of outputting an index value or the like is not limited to output on a display.

In each of the embodiments, a case in which the organ is a liver and a main bifurcation is a portal vein is used as an example. However, the present invention is not limited to assistance in a surgery of a liver. The present invention is applicable to assistance in a surgery of other organs, such as a lung.

The present invention is not limited to the embodiments of the present application, and various modifications are possible without departing from the gist of the present invention.

What is claimed is:

1. A surgery-assistance apparatus that sets a margin region with respect to a target region of excision in an organ including a diseased part to be removed, and the margin region being removed together with the target region, the apparatus comprising:

a medical image obtainment unit that obtains a medical image representing the organ including the diseased part to be removed;

an organ region extraction unit that extracts an organ region from the obtained medical image;

a structure region extraction unit that extracts, from the obtained medical image, a structure region representing a structure that dominates the organ and that is a tree structure;

a target region determination unit that specifies each part of the structure which dominates each voxel in the organ region respectively, receives a manual input specifying a predetermined position at which the structure is to be removed, determines a dominance region in the organ as the target region, and a region in the organ other than the target region, as a non-target region, and wherein the dominance region comprises all voxels being dominated by a part of the structure, the part of which extends from the predetermined position in the structure region toward a part of the organ, the part of the organ including the diseased part; and a margin region setting unit that sets, based on a distance from the predetermined position to each position on a boundary surface between the target region and the non-target region, the margin region to be added to the target region, wherein the margin region setting unit sets the margin region in such a manner that the width of the margin region gradually increases from zero to a predetermined value while increasing the distance in a range in which the distance is less than or equal to a predetermined threshold value, and that the width of the margin region is the predetermined value in a range in which the distance is greater than the predetermined threshold value.

2. A surgery-assistance apparatus, as defined in claim 1, further comprising:

a display control unit that makes a display device display the set margin region in an identifiable manner.

3. A surgery-assistance apparatus, as defined in claim 1, further comprising:

a detection unit that detects the structure region included in the set margin region other than the part of the structure.

4. A surgery-assistance apparatus, as defined in claim 3, further comprising:

a display control unit that makes a display device display, in an identifiable manner, the detected structure region included in the set margin region other than the part of the structure.

5. A surgery-assistance apparatus, as defined in claim 3, further comprising:

a warning unit that gives a warning based on detection of the structure region included in the set margin region other than the part of the structure.

6. A surgery-assistance apparatus, as defined in claim 1, wherein the organ is a liver and the structure is a blood vessel.

7. A surgery-assistance apparatus, as defined in claim 1, wherein the organ is a lung and the structure is a bronchus.

8. A surgery-assistance method for setting a margin region to be added to a target region of excision in an organ including a diseased part to be removed, the method comprising the steps of:

obtaining a medical image representing the organ including the diseased part to be removed;

extracting an organ region from the obtained medical image;

extracting, from the obtained medical image, a structure region representing a structure that dominates the organ and that is a tree structure;

specifying each part of the structure which dominates each voxel in the organ region respectively, receives a manual input specifying a predetermined position at which the structure is to be removed, determining a dominance region in the organ as the target region, and a region in the organ other than the target region, as a non-target region, and wherein the dominance region comprises all voxels being dominated by a part of the structure, the part of which extends from the predetermined position in the structure region toward a part of the organ, the part of the organ including the diseased part; and setting, based on a distance from the predetermined position to each position on a boundary surface between the target region and the non-target region, the margin region to be added to the target region, wherein the margin region is set in such a manner that the width of the margin region gradually increases from zero to a predetermined value while increasing the distance in a range in which the distance is less than or equal to a predetermined threshold value, and that the width of the margin region is the predetermined value in a range in which the distance is greater than the predetermined threshold value.

9. A non-transitory computer-readable recording medium having stored therein a surgery-assistance program for causing a computer to execute processing for setting a margin region to be added to a target region of excision in an organ including a diseased part to be removed, the program comprising the procedures of:

obtaining a medical image representing the organ including the diseased part to be removed;

extracting an organ region from the obtained medical image;

extracting, from the obtained medical image, a structure region representing a structure that dominates the organ and that is a tree structure;

specifying each part of the structure which dominates each voxel in the organ region respectively, receives a manual input specifying a predetermined position at which the structure is to be removed, determining a dominance region in the organ as the target region, and a region of the organ other than the target region, as a non-target region, and wherein the dominance region comprises all voxels being dominated by a part of the structure, the part of which extends from the predetermined position in the structure region toward a part of the organ, the part of the organ including the diseased part; and setting, based on a distance from the predetermined position to each position on a boundary surface between the target region and the non-target region, the margin region to be added to the target region, wherein the margin region is set in such a manner that the width of the margin region gradually increases from zero to a predetermined value while increasing the distance in a range in which the distance is less than or equal to a predetermined threshold value, and that the width of the margin region is the predetermined value in a range in which the distance is greater than the predetermined threshold value.

10. A surgery-assistance apparatus that sets a margin region with respect to a target region of excision in an organ including a diseased part to be removed, and the margin region being removed together with the target region, the apparatus comprising:

a medical image obtainment unit that obtains a medical image representing the organ including the diseased part to be removed;

an organ region extraction unit that extracts an organ region from the obtained medical image;

a structure region extraction unit that extracts, from the obtained medical image, a structure region representing a structure that dominates the organ and that is a tree structure;

a target region determination unit that specifies each part of the structure which dominates each voxel in the organ region respectively, determines a dominance region in the organ as the target region, and a region in the organ other than the target region, as a non-target region, and wherein the dominance region comprises all voxels being dominated by a part of the structure, the part of which extends from a predetermined position in the structure region toward a part of the organ, the part of the organ including the diseased part; and a margin region setting unit that sets, based on a distance from the predetermined position to each position on a boundary surface between the target region and the non-target region, the margin region to be added to the target region, wherein the margin region setting unit sets the margin region in such a manner that the width of the margin region gradually increases from zero to a predetermined value while increasing the distance in a range in which the distance is less than or equal to a predetermined threshold value, and that the width of the margin region is the predetermined value in a range in which the distance is greater than the predetermined threshold value, and wherein the margin region setting unit sets the width of the margin region in such a manner that the width of the margin region increases in proportion to a distance from zero to a predetermined value with increasing the distance in a range in which the distance is less than or equal to a predetermined threshold value, and such that the width of the margin region is the predetermined value in a range in which the distance is greater than the predetermined threshold value $$M(pt) = \begin{cases} \left(1 - \dfrac{D(pt, v)}{r}\right) \times M, & (D(pt, v) < r) \\ M, & (r \le D(pt, v)) \end{cases}.$$

11. A surgery-assistance apparatus that sets a margin region with respect to a target region of excision in an organ including a diseased part to be removed, and the margin region being removed together with the target region, the apparatus comprising:

a medical image obtainment unit that obtains a medical image representing the organ including the diseased part to be removed;

an organ region extraction unit that extracts an organ region from the obtained medical image;

a structure region extraction unit that extracts, from the obtained medical image, a structure region representing a structure that dominates the organ and that is a tree structure;

a target region determination unit that specifies each part of the structure which dominates each voxel in the organ region respectively, determines a dominance region in the organ as the target region, and a region in the organ other than the target region, as a non-target region, and wherein the dominance region comprises all voxels being dominated by a part of the structure, the part of which extends from a predetermined position in the structure region toward a part of the organ, the part of the organ including the diseased part; and a margin region setting unit that sets, based on a distance from the predetermined position to each position on a boundary surface between the target region and the non-target region, the margin region to be added to the target region, wherein the margin region setting unit sets the margin region in such a manner that the width of the margin region gradually increases from zero to a predetermined value while increasing the distance in a range in which the distance is less than or equal to a predetermined threshold value, and that the width of the margin region is the predetermined value in a range in which the distance is greater than the predetermined threshold value, wherein the apparatus further comprises a detection unit that detects the structure region included in the set margin region other than the part of the structure, and wherein the target region determination unit determines, as the target region, both of the dominance region dominated by the part of the structure and a dominance region that comprises all voxels being dominated by the detected structure region included in the set margin region other than the part of the structure.

* * * * *